United States Patent [19]

Ripple

[11] 4,186,157
[45] * Jan. 29, 1980

[54] PHOSPHORUS-CONTAINING REACTION MIXTURE

[75] Inventor: David E. Ripple, Kirtland, Ohio

[73] Assignee: The Lubrizol Corporation, Wickliffe, Ohio

[*] Notice: The portion of the term of this patent subsequent to Mar. 28, 1995, has been disclaimed.

[21] Appl. No.: 873,298

[22] Filed: Jan. 30, 1978

Related U.S. Application Data

[62] Division of Ser. No. 781,249, Mar. 25, 1977, Pat. No. 4,081,387.

[51] Int. Cl.$^2$ .................. C07F 9/165; C10M 1/48
[52] U.S. Cl. ..................... 260/948; 260/968
[58] Field of Search ............. 260/948, 929, 968

[56] References Cited
U.S. PATENT DOCUMENTS 4,081,387  3/1978  Ripple ................. 260/948 X Primary Examiner—Anton H. Sutto
Attorney, Agent, or Firm—James W. Adams, Jr.

[57] ABSTRACT

A process for the preparation of a phosphorus-containing reaction mixture comprising at least one additive corresponding to the formula:

$$Y^a\text{-}S\text{-}Y^b$$

wherein $Y^a$ corresponds to $$\begin{array}{c} R^1 \\ \diagdown \\ R^2 \diagup \end{array} \!\!\! P \!\!\! \begin{array}{c} \diagup\!\!\!\!X \\ \diagdown X\text{—}CH\text{—}Z \\ | \\ R^3 \end{array}$$

and Z is $$\begin{array}{c} R^4 \\ | \\ -CH \end{array}\!\!\!\left(\begin{array}{c} R^5 \\ | \\ C \\ | \\ R^6 \end{array}\right)_n\!\!\!\begin{array}{c} OH \\ | \\ C\!\!-\!\!, \\ | \\ R^7 \end{array}$$

$$\begin{array}{c} -CH\!=\!C\!- \\ | \\ R^7 \end{array},$$

or $$\begin{array}{c} R^4 \\ | \\ -CH \end{array}\!\!\!\left(\begin{array}{c} R^5 \\ | \\ C \\ | \\ R^6 \end{array}\right)_{n'}\!\!\!\!-CH\!=\!C\!-; \\ | \\ R^7 \end{array}$$

$Y^b$ is $$-R^8\text{-}S\text{-}R^9$$

or $$-R^8\text{-}H$$

which comprises the steps of reacting
(A) at least one phosphorus-containing reactant corresponding to the formula:

$$\begin{array}{c} R^1 \\ \diagdown \\ R^2 \diagup \end{array} \!\!\! P \!\!\! \begin{array}{c} \diagup\!\!\!\!X \\ \diagdown X\text{—}H \end{array}$$

with
(B) at least one unsaturated aldehyde or ketone corresponding to the formula:

$$R^3\text{—}CH\!=\!C\!\!\!\left(\begin{array}{c} R^4 \\ | \\ \\ | \end{array}\!\!\!\left(\begin{array}{c} R^5 \\ | \\ C \\ | \\ R^6 \end{array}\right)_n\!\!\!\begin{array}{c} O \\ \| \\ C\text{—}R^7 \end{array}\right.$$

with
(C) at least one thiol or dithiol corresponding to the formula:

$$HS\text{-}R^8\text{-}H$$

or is $$HS\text{-}R^8\text{-}SH$$

wherein each $R^1$ and $R^2$ is independently a member selected from the group consisting of hydrocarbyl, hydrocarbyloxy and hydrocarbylmercapto of one to about 30 carbon atoms; $R^3$ is hydrogen or hydrocarbyl of up to about 10 carbon atoms; $R^4$ is hydrogen or lower alkyl; $R^5$ and $R^6$ are each independently selected from hydrogen, hydrocarbyl, hydrocarbyloxy and hydrocarbylmercapto of one to about 10 carbon atoms; $R^7$ is hydrogen or hydrocarbyl of one to about 30 carbon atoms; $R^8$ is a divalent hydrocarbyl group of one to about 30 carbon atoms; $R^9$ is hydrogen or $Y^a$; and each X is independently oxygen or divalent sulfur; n is zero or an integer of one to about 10; and n' is zero or an integer of one to about 9.

The phosphorus-containing reaction mixture has increased resistance to oxidative degradation and antiwear properties in lubricant compositions.

17 Claims, No Drawings

PHOSPHORUS-CONTAINING REACTION MIXTURE

REFERENCE TO RELATED APPLICATIONS

This application is a divisional of U.S. Application Ser. No. 781,249 filed Mar. 25, 1977 now U.S. Pat. No. 4,081,387.

It is known in the prior art that certain phosphorus acid compounds can be reacted with certain unsaturated aldehydes or ketones to form adducts. These adducts can be used in lubricant compositions as antioxidants and corrosion inhibitors and for imparting antiwear and load-carrying characteristics to lubricating oils. (See, for example, U.S. Pat. Nos. 2,632,020; 2,794,041; 2,846,245; 2,948,682 and 3,644,206.)

It has not been previously known or suggested, however, that these adducts be further reacted with certain thiols or dithiols to form the additives of this invention or to incorporate these additives in lubricant and functional fluid compositions such as those of the present invention.

This invention relates to new compositions of matter and to lubricating and functional fluids containing them. More particularly, the compositions of this invention are additives made by the reaction of certain phosphorus acid compounds with certain aldehydes or ketones and certain thiols or dithiols. This invention also relates to lubricant and hydraulic fluid compositions comprising these additives as well as processes for preparing these additives.

More specifically the compounds of the present invention correspond to the formula:

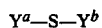

wherein $Y^a$ corresponds to

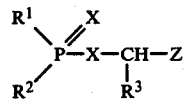

and Z is

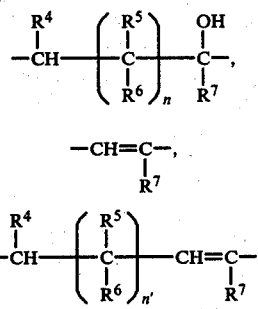

wherein each $R^1$ and $R^2$ is independently a member selected from the group consisting of hydrocarbyl, hydrocarbyloxy and hydrocarbyl mercapto of one to about 30 carbon atoms; $R^3$ is hydrogen or hydrocarbyl of up to about 10 carbon atoms; $R^4$ is hydrogen or lower alkyl; $R^5$ and $R^6$ are each independently selected from hydrogen, hydrocarbyl, hydrocarbyloxy and hydrocarbylmercapto of one to about 10 carbon atoms; $R^7$ is hydrogen or hydrocarbyl of one to about 30 carbon atoms; each X is independently oxygen or divalent sulfur; n is zero or an integer of one to about 10; n' is zero or an integer of one to about 9; $Y^b$ is

or

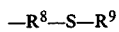

wherein $R^8$ is a divalent hydrocarbyl group of one to about 30 carbon atoms and $R^9$ is hydrogen or $Y^a$.

The phosphorus acid compounds used in the preparation of the additive compositions of the present invention are of the formula:

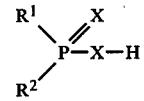

wherein each X is independently oxygen or divalent sulfur and $R^1$ and $R^2$ are each independently a member selected from the group consisting of hydrocarbyl, hydrocarbyloxy and hydrocarbylmercapto of one to about 30 carbon atoms. Preferably, X is oxygen and each $R^1$ and $R^2$ contains between one to about 18 carbon atoms; more preferably both $R^1$ and $R^2$ are independently alkoxy or alkylphenoxy groups containing one to about 18 carbon atoms and each X is a divalent sulfur atom.

When reference is made in this specification and in the appended claims to the term "lower" in conjunction with another group such as lower alkyl, lower alkoxy, lower alkylmercapto, and the like, it is intended to include all such groups having a total carbon content of up to seven. For example, "lower alkyl" includes all straight and branched chain alkyl groups of up to seven carbon atoms such as methyl, ethyl, propyl, isopropyl, tert-butyl, n-heptyl, etc.

When reference is made in this specification and the appended claims to hydrocarbyl, hydrocarbyloxy, hydrocarbylmercapto, aliphatic or alkyl groups, it is to be understood, unless expressly stated to the contrary, that analogous substituted groups referred to as substantially hydrocarbyl, substantially hydrocarbyloxy, substantially hydrocarbylmercapto, substantially aliphatic, and substantially alkyl groups are also contemplated. The description of these groups as being substantially hydrocarbyl means that they do not contain any non-hydrocarbyl substituents which would significantly alter the general hydrocarbyl characteristics or properties of the group relevant to their uses as described herein. Thus, it is obvious in the context of this invention, for example, that a purely hydrocarbyl $C_{20}$ alkyl group and a $C_{20}$ alkyl group substituted with a methyl mercapto or methoxyl substituent at a point in the chain remote from other polar (i.e., non-hydrocarbyl) groups, would be substantially equivalent in its properties with regard to its use in this invention and would, in fact, be recognized as substantially equivalent by those of ordinary skill in the art. That is, one of ordinary skill in the art would recognize both such groups to be substantially hydrocarbyl, etc.

Non-limiting examples of substituents which do not significantly alter the hydrocarbyl, etc., properties or nature of hydrocarbyl, etc., groups of this invention are the following:

Ether groups (especially hydrocarbyloxy and particularly alkoxy groups of up to ten carbon atoms)

Amino groups (including mono- and disubstituted amino groups such as mono- and dialkyl amino or mono- and diaryl amino and the like, e.g., ethyl amino, dimethyl amino, diheptyl amino, cyclohexyl amino, benzyl amino, etc.)

Oxo groups (e.g.,

such as in ketones and aldehydes)

Oxa groups (e.g., —O— linkage in the main carbon chain)

Nitro groups

Imino groups (e.g.,

linkage in the main carbon chain)

Cyano groups

Fluoro groups

Chloro groups

Thioether groups (especially $C_{1-10}$ alkyl thioether)

Thia groups (e.g., —S— linkage in the main carbon chain)

Carbohydrocarbyloxy groups (e.g.,

hydrocarbyl)

Sulfonyl groups

Sulfinyl groups.

This list is intended to be merely illustrative and not exhaustive and the omission of a certain class of substituent is not meant to require its exclusion.

In general, if such substituents are present, there will not be more than two for each 10 carbon atoms in the hydrocarbyl groups and preferably not more than one for each 10 carbon atoms. Usually, the hydrocarbyl, hydrocarbyloxy, hydrocarbylmercapto, etc., groups will be free from any non-hydrocarbon groups due to economic considerations; that is, they will be characterized by the presence of only purely hydrocarbyl groups which have only carbon and hydrogen atoms.

In the above formula, $R^1$ and $R^2$ can be saturated or ethylenically unsaturated and include alkyl, alkenyl, cycloalkyl, cycloalkenyl, aryl arylalkyl, alkylaryl, etc. Suitable specific groups include methyl, ethyl n-propyl, isopropyl, n-butyl, isobutyl, amyl, isoamyl, n-hexyl, 2-ethylhexyl, 4-methyl-2-pentyl, allyl, 3-octenyl, cyclohexyl, chlorocyclohexyl, methylcyclohexyl, heptyl, n-octyl, isooctyl, tertiary octyl, nonyl, decyl, lauryl, cetyl, phenyl, bromophenyl, 2,4-dichlorophenylethyl, chlorophenyl, nitrophenyl, methoxyphenyl, ethylphenyl, propylphenyl, butylphenyl, alkylated phenyl such as propylene tetramer substituted phenyl, benzylphenylethyl, octenyl, cyclohexenyl, ethylcyclopentyl, N,N'-dibutylaminopropylphenyl, 3-nitrooctyl, p-carboxyphenyl, phenoxyphenyl, naphthyl, alkylated naphthyl such as propylene tetramer substituted naphthyl, acetylphenyl, 2-ethoxyethyl, 6-ethylaminoheptyl, 4-cyanophenyl, 3,3,3-trifluoropropyl, dichloromethyl-3-thia-n-octyl, 2-methylmercapto naphthyl, 4-ethyl sulfonyl-n-butyl, 4-phenylsulfinyl, phenyl, etc.

Methods for the preparation of such phosphorus acid compounds are well-known to those of skill in the art and need not be repeated here. For convenience, however, reference is made to "Organophosphorus Compounds" by G. M. Kosolapoff, John Wiley Publishers, 1950, N.Y., which is incorporated herein by reference for its disclosure of methods for preparing the phosphorus acid compounds. The following U.S. Pat. Nos. are also incorporated by reference for their disclosure of methods for preparing the phosphorus acid compounds: 2,480,673; 2,552,570; 2,618,597; 2,734,864; 2,734,865; 2,977,382; 3,000,822; 3,058,910; 3,070,546; 3,073,781; 3,029,268; 3,081,261; 3,151,075; 3,361,668; 3,185,728; 3,197,496; 3,210,275; 3,293,181 and 3,442,804.

A particularly preferred type of phosphorus acid compound useful in this invention is prepared by the reaction of phosphorus pentasulfide or homologs thereof (e.g., $P_4S_{10}$) with one or more hydroxy compounds which contain the organic groups $R^1$ and $R^2$ as defined above; that is, $R^1OH$ and $R^2OH$ or mixtures of two or more of any of these. An example of this type of reaction is the reaction of phosphorus pentasulfide with ethyl alcohol to produce, O,O-diethyl phosphorodithioic acid.

The aldehydes and ketones used in this invention are of the formula:

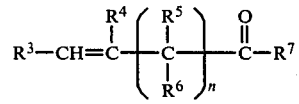

wherein $R^3$ is hydrogen or hydrocarbyl of up to about 10 ten carbon atoms; $R^4$ is hydrogen or lower alkyl; $R^5$ and $R^6$ are each independently selected from hydrogen, hydrocarbyl, hydrocarbyloxy and hydrocarbylmercapto of one to about 10 carbon atoms; $R^7$ is hydrogen or hydrocarbyl of one to about 30 carbon atoms and n is zero or an integer of one to about 10.

Examples of the preferred aldehydes which can be used in this invention include: acrolein, crotonaldehyde, 2-pentenal, 3-octenal, 5-decenal, 2-ethyl-2-hexenal, 10-hexadecenal, methacrolein and cinnamaldehyde. Because of their commercial availability, acrolein and crotonaldehyde are especially applicable.

Examples of the preferred ketones which can be used in this invention include: methylvinylketone, methylisopropenylketone, methylpropenylketone, mesityl oxide, 5-hexen-2-one, 5-methyl-5-hexen-2-one, 5-hepten-2-one and 3-hepten-2-one.

It is often desirable to use a freshly distilled unsaturated aldehyde or ketone containing none to about 2.0% by weight, preferably, none to about 0.5% by weight of a polymerization inhibitor such as hydroquinone, di-tertiary-butyl catechol, 2,6-di-tertiary-butylphenol, etc.

In carrying out the reaction of the phosphorus acid and unsaturated aldehyde or ketone to form the adduct, the reactants are brought together by contacting about 0.1 to about 1.0 equivalent of at least one of the aforedescribed phosphorus acid compounds (One equivalent of phosphorus acid is the molecular weight of potassium hydroxide, expressed in milligrams, divided by the acid number of the phosphorus acid compound. The acid number is the quantity of potassium hydroxide, expressed in milligrams, that is required to titrate the strong acid constituents present in one gram of sample.) with about 1.2 to about 0.1 equivalent of the afore-described unsaturated aldehydes or ketones (One equivalent of unsaturated aldehyde or ketone is the molecular weight divided by the number of oxo groups present.). The reaction is normally carried out for a period of about 0.1 to about 24 hours, generally, about 0.1 to about 5 hours, at a temperature in the range of about 10° C. up to the decomposition point of any component of the reaction mixture, preferably from about 10° C. to about 100° C.

Suitable substantially inert organic liquid solvent/diluents may be used in the reaction and include such relatively low boiling saturated hydrocarbons in aromatic liquids as hexane, heptane, benzene, toluene, xylene, etc., as well as high boiling materials such as solvent neutral oils, bright stocks and various types of synthetic and natural lubricating oil base stocks.

As used in the specification and the appended claims, the term "substantially inert" when used to refer to solvents, diluents, and the like, is intended to mean that the solvent, diluent, etc., is inert to chemical or physical change under the conditions in which it is used so as not to materially interfere in an adverse manner with the preparation, storage, blending and/or functioning of the compositions, additive, compound, etc. of this invention in the context of its intended use. For example, small amounts of a solvent, diluent, etc. can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Substantially inert" as used herein is, thus, readily understood and apreciated by those of ordinary skill in the art.

While the reactants can be combined in any order to make the above-mentioned phosphorus acid:unsaturated aldehyde or ketone adduct, it is preferable to add the unsaturated aldehyde or ketone to the phosphorus acid compound. Suitable agitation of the reaction mixture is desirable, particularly when two liquid phases are present.

The reaction is often carried out in the absence of added catalysts and/or in the presence of an inert atmosphere. The progress of the reaction may be followed by determination of the acidity of the reaction mixture which drops to a low value as free acid is converted to neutral ester.

It is often found, however, that the acidity of the reaction mixture cannot be reduced below an acid range of about 3 to about 15 even though more unsaturated aldehyde or ketone is added. Therefore, it is often preferred that if the determination of the acidity of the reaction mixture containing the adduct is in the acid range of about 3 to about 15, that another reactant be employed. In this instance epoxides of up to about 22 carbon atoms such as ethylene oxide, propylene oxide, butylene oxide, styrene oxide and others can be used. Generally, the lower alkylene oxides such as ethylene oxide and propylene oxide are used. The epoxide reduces the acidity of the reaction mixture further by converting free acid into neutral ester. The amount of epoxide used ranges from none to about 1.0 equivalent (One equivalent of epoxide is the molecular weight divided by the number of epoxy groups, e.g.,

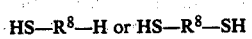

present), preferably from none to about 0.2 equivalent. The epoxide addition is normally carried out for a period of about 0.01 to about 1 hour, generally, about 0.01 to about 0.1 hour at a temperature over the range of about 25° C. up to the decomposition point of any component of the reaction mixture, preferably, from about 25° C. to about 70° C.

The thiols or dithiols used in this invention with the above-mentioned phosphorus acid:unsaturated aldehyde or ketone adducts are of the formula:

$$HS-R^8-H \text{ or } HS-R^8-SH$$

wherein $R^8$ is a hydrocarbyl group of one to about 30 carbon atoms. Preferably, $R^8$ contains between one and 18 carbon atoms; more preferably, $R^8$ is a saturated hydrocarbon containing up to 12 carbon atoms.

Examples of the mercaptans which can be used in this invention include: methanethiol, ethanethiol, 2-propanethiol, 1-propanethiol, 2-methyl-2-propanethiol, 2-butanethiol, 2-methyl-1-propanethiol, 1-butanethiol, 1-pentanethiol, 1-hexanethiol, 1-heptanethiol, 1-octanethiol, n-dodecanethiol, t-dodecanethiol, cyclohexanethiol, 1,2-ethanedithiol, benzenethiol, and t-benzenedithiol.

In carrying out the reaction of the phosphorus acid:unsaturated aldehyde or ketone adducts with the aforedescribed thiol or dithiol, the reactants are brought together by contacting about 0.1 to about 1.0 equivalent of at least one of the previously described phosphorus acid:unsaturated aldehyde or ketone adducts (One equivalent of the phosphorus acid:unsaturated aldehyde or ketone adduct is the molecular weight divided by the number of oxo groups present.) with about 1.2 to about 0.1 equivalent of the previously described thiol or dithiol (One equivalent of thiol or dithiol is the molecular weight divided by the number of mercapto groups present.) in the presence of an acid catalyst; that is, a strong organic acid or a mineral acid such as para-toluene sulfonic acid, dithiophosphoric acid, Super Filtrol (a commercially available acidified clay), hydrochloric acid, etc. at a temperature in the range of about 0° C. to about 100° C. The reaction is normally carried out for a period of about 0.1 to about 24 hours, generally, about 0.1 to about 6 hours.

Suitable substantially inert organic liquid solvent/diluents can be used in the reaction and include such relatively low boiling saturated hydrocarbons or aromatic liquids as hexane, heptane, benzene, toluene, xylene, etc., as well as high boiling materials such as solvent neutral oils, bright stocks and various types of synthetic and natural lubricating oil base stocks. Factors governing the choice and use of such materials are well-known to those of skill in the art. Normally, such a diluent will be used to facilitate heat control, handling, filtration, etc. It is often desirable to select a diluent which will be compatible with the other materials which are to be present in the environment where the product is intended to be used.

The inventive additives can be recovered from such solvent/diluents by such standard procedures as distillation, evaporation, precipitation, crystallization, dialysis, etc., when desired. Alternatively, if the solvent/diluents are, for example, a base oil suitable for use in the functional fluid compositions of this invention, the product can be left in the solvent/diluents and used to form the lubricating or functional fluid composition as described below.

The above-mentioned phosphorus acid:unsaturated aldehyde or ketone adduct, thiol or dithiol, acid catalyst and, optionally, solvent/diluents are combined and suitable agitation of the reaction mixture is desirable. The reaction mixture is held at room temperature up to reflux temperature and the extent of the reaction of the thiol or dithiol with the adduct can be followed by analytical determination of the percent unreacted mercaptan remaining in the reaction mixture. When the reaction is essentially complete, the reaction mixture can be stripped under a vacuum up to about 100° C. to remove the solvent/diluent (if such a relatively low boiling solvent/diluent is used in the reaction) and then filtered through diatomaceous earth to give the desired saturated phosphorus-containing composition.

To prepare the unsaturated phosphorus-containing composition, the phosphorus acid:unsaturated aldehyde or ketone adduct, thiol or dithiol and, optionally, solvent/diluents are combined and the reaction is carried out in the presence of an acid catalyst; that is, a strong organic acid or a mineral acid. Examples of suitable acid catalysts are para-toluene sulfonic acid, dithiophosphoric acid, Super Filtrol (a commercially available acidified clay), hydrochloric acid, etc. The reaction mixture is held at about room temperature up to reflux temperature and the extent of the reaction of the thiol or dithiol with the adduct can be followed by analytical determination of the percent unreacted mercaptan remaining in the reaction mixture. The water of reaction is removed by azeotroping during the reaction. The reaction mixture can be stripped under a vacuum up to about 100° C. to remove the solvent/diluent (if such a relatively low boiling solvent/diluent is used in the reaction) and then filtered through diatomaceous earth to give the desired composition.

Additionally, about 0.1 to about 4.0 moles of sulfur flowers can be mixed with about 1.0 to about 0.1 mole of the unsaturated phosphorus-containing composition derived from the reaction, in the presence of an acid catalyst as mentioned above, of a phosphorus acid compound with an unsaturated aldehyde or ketone and with a thiol or dithiol and removal of the water of reaction. The reaction is normally carried out for a period of about 0.1 to about 24 hours, generally, about 0.1 to about 4 hours, at a temperature in the range of about 110° C. up to the decomposition of the reaction mixture, preferably from about 160° C. to about 220° C. This additional sulfur treatment of the phosphorus-containing compositions, as described above, enhances lubricant compositions by imparting additional antiwear and load-carrying properties to lubricant oils.

The following non-limiting examples are specific preferred embodiments of the present invention. All references to percentages, parts, etc., in the present specification and appended claims refer to percentages, parts, etc., by weight unless expressly stated otherwise.

EXAMPLE 1

A phosphorodithioic dialkylaryl acid is prepared by reacting at a temperature of about 149°–154° C. one mole $P_2S_5$ with 4 moles of a propylene tetramer alkylated phenol. The resulting acid is characterized by a phosphorus content of 4.70%, a sulfer content of 9.63% and an acid neutralization number to bromophenol blue (i.e., NNA(bpb)), as determined by ASTM Procedure D-974, of 80.

EXAMPLE 2

Freshly distilled acrolein (57 grams, 1.01 equivalents) is added to the phosphorodithioic dialkylaryl acid (643 grams, 0.92 equivalent) as prepared in Example 1 under a nitrogen purge over a one-hour period at about 60°–70° C. The material is then held at about 70° C. for 3 hours, cooled to room temperature and is characterized by a NNA(bpb) of 6. The material is then stripped to about 80° C. under a vacuum of 20 torr. The stripped material is then maintained at about 60° C. while propylene oxide (7 grams, 0.12 mole) is added. The material is filtered through diatomaceous earth. The filtrate is characterized by a phosphorus content of 4.37%, a carbonyl content of 2.81% and a NNA(bpb) of 6.

EXAMPLE 3

Textile spirits (100 ml), an aliphatic petroleum naphtha having a distillation range of 63°–79° C. at 760 torr, n-dodecylmercaptan (12 grams, 0.06 equivalent), the product of Example 2 (60 grams, 0.06 equivalent), 0.1 gram paratoluene sulfonic acid and 11 grams Linde 3A molecular sieve pellets are held at about 25°–30° C. for 20 hours. The material is filtered through paper to remove the sieves, stripped to about 80° C. under a vacuum of 30 torr and then filtered through diatomaceous earth. The product is characterized by a sulfur content of 10.25%, a phosphorus content of 3.49% and a NNA(bpb) of 3.

EXAMPLE 4

A phosphorodithioic dialkyl acid is prepared by reacting at a temperature of about 110°–118° C. one mole $P_2S_5$ with 4 moles of decyl alcohol:isooctyl alcohol in a (30:70) weight ratio. The resulting acid is characterized by a phosphorus content of 7.9%, a sulfur content of 16.2% and a NNA(bpb) of 131.

EXAMPLE 5

Freshly distilled acrolein (130 grams, 2.33 equivalents) is added to the phosphorodithioic dialkyl acid (905 grams, 2.12 equivalents) as prepared in Example 4 under a nitrogen purge over a one-hour period at about 60°–70° C. The material is held at about 60°–70° C. for 3.5 hours, cooled to room temperature and is characterized by a NNA(bpb) of 5. The material is then stripped to about 48° C. under a vacuum of 24 torr. At about 40° C. propylene oxide (10 grams, 0.17 equivalent) is added and the material is filtered through diatomaceous earth. The filtrate is characterized by a phosphorus content of 5.80%, a carbonyl content of 5.43% and a NNA(bpb) of 1.2.

EXAMPLE 6

Benzene (200 ml), the product of Example 5 (229 grams, 0.48 mole), n-dodecylmercaptan (97 grams, 0.48 mole) and 0.5 gram para-toluene sulfonic acid is held at reflux, removing by azeotroping, 58% of the theory water. The material is stripped to about 90° C. under a vacuum of 28 torr and then filtered through diatomaceous earth. The filtrate is characterized by a sulfur content of 14.7%, a phosphorus content of 4.98%, a carbonyl content of 1.33%, a mercaptan content of 2.25% and a NNA(bpb) of 4.5.

EXAMPLE 7

Sulfur flowers (2.6 grams, 0.08 mole) and the product of Example 3 (47 grams, 0.04 mole) is held at about 185°–190° C. for 2 hours. The material is cooled to about 80° C., purged with nitrogen and then filtered through diatomaceous earth. The product is characterized by a sulfur content of 12.1%.

EXAMPLE 8

The procedure of Example 2 is followed except freshly distilled crotonaldehyde (71 grams, 1.01 equivalents) is substituted for the acrolein.

EXAMPLE 9

The procedure of Example 6 is followed except freshly distilled crotonaldehyde (164 grams, 2.33 equivalents) is substituted for the acrolein.

EXAMPLES 10 AND 11

In the same manner as in Example 5, freshly distilled crotonaldehyde and methylvinyl ketone is substituted for the acrolein on the same molar basis, respectively, to form the desired intermediates.

EXAMPLES 12 AND 13

The intermediates of Examples 10 and 11 are further reacted by following the procedure as described in Example 6 to form the desired products.

EXAMPLE 14

The procedure of Example 6 is followed except 1,2-ethanedithiol (24 grams, 0.24 equivalent) is substituted for the n-dodecylmercaptan.

Although the phosphorus-containing compositions of this invention as described above are, in themselves, useful as extreme pressure, anti-wear and load-carrying agents, they are nevertheless susceptible to improvement by the addition of one or more chemical additives to supplement their action to give the properties desired when incorporated into the lubricating and hydraulic compositions of this invention. Such supplemental agents may be illustrated by the lead, nickel or Group IIA and IIB metal phosphorodithioate salts in which the metal may be magnesium, calcium, barium, strontium, zinc, cadmium, lead or nickel. Zinc phosphorodithioates are particularly preferred. Other types of extreme pressure agents which can find use in the lubricating oil compositions of this invention include chlorinated waxes, sulfurized or phosphosulfurized fatty acid esters, di- or trihydrocarbyl phosphites and phosphates, dihydrocarbon polysulfides and metal dithiocarbamates. These and other useful extreme pressure agents are described in more detail in the books both entitled "Lubricant Additives" by Smith and Smalheer (published by the Lezius-Hiles Co., of Cleveland, Ohio) and by M. W. Raney (published by the Noyes Data Corporation of Park Ridge, New Jersey) pages 146–212, both of which are incorporated herein by reference for their disclosure of additional extreme pressure agents which can be used in conjunction with the additives of the present invention.

Still another type of additive which can be useful in the lubricating oil compositions of the present invention is one or more rust-inhibiting agents. A very effective rust-inhibiting agent is the alkyl or alkenyl-substituted acids having the structure

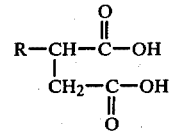

in which R is a hydrocarbon radical having at least 10 carbon atoms. Preferably, R is a dodecenyl group. When a rust-inhibiting agent is used in the lubricant compositions of this invention only a small amount is needed. It can be as little as about 0.01 part and seldom exceeds about 2 parts per 100 parts of the lubricant composition.

Demulsifiers may also be included in the lubricant compositions of this invention. The preferred demulsifiers are the commercial alkylated phenoxypoly(alkyleneoxy)alkanol compounds such as nonylphenoxypoly(ethyleneoxy)ethanol. Generally, the amount of demulsifier used can be as little as about 0.01 part and seldom exceeds about 2 parts per 100 parts of the lubricant composition.

The lubricant compositions of this invention can also contain a conventional foam inhibitor such as a commercial dialkyl siloxane polymer.

Oxidation inhibitors can also be included in the lubricating oil compositions of this invention. Hindered phenols such as 2,4-di-t-butyl-6-methylphenol, 4,4'-methylene-(2,6-di-t-pentylphenol), and 2,6-di-t-octyl-4-secondary butylphenol are representative of useful oxidation inhibitors. The concentration of such oxidation inhibitors in the lubricating oil compositions of this invention is usually between about 0.01 to about 2 parts per 100 parts of the lubricant composition.

The phosphorus-containing compounds of this invention can be effectively employed in a variety of lubricating compositions based on diverse oils of lubricating viscosity such as natural or synthetic lubricating oils, or suitable mixtures thereof. The lubricating compositions contemplated include principally crankcase lubricating oils for spark-ignited and compression-ignited internal combustion engines including automobile and truck engines, two-cycle engine lubricants, aviation piston engines, marine and railroad diesel engines, and the like. However, automatic transmission fluids, transaxle lubricants, gear lubricants, metal-working lubricants, hydraulic fluids, and other lubricating oil and grease compositions can benefit from the incorporation of the present phosphorus-containing compounds.

Natural oils include animal oils and vegetable oils (e.g., castor oil, lard oil) as well as solvent-refined or acid-refined mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylene, propylene/isobutylene copolymers, chlorinated polybutylenes, etc.); alkylbenzenes (e.g., dodecylbenzenes, tetradecylbenzenes, dinonylbenzenes, di-(2-ethylhexyl)benzenes, etc.); polyphenyls (e.g., biphenyls, terphenyls, etc.); and the like. Alkylene oxide polymers and interpolymers and derivatives thereof, where the terminal hydroxy groups have been modified by esterification, etherification, etc., constitute another class of known synthetic lubricating oils. These are exemplified by the oils prepared through polymerization of ethylene oxide or propylene oxide, the alkyl and aryl ethers of these polyoxyalkylene polymers (e.g., methyl polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol. Another suitable class of synthetic lubricating oils comprises the esters of dicarboxylic acid (e.g., phthalic acid, succinic acid, maleic acid, azeleic acid, suberic acid, sebacic acid, fumaric acid, linoleic acid dimer, etc.) with a variety of alcohols, (e.g., butyl alcohol, hexyl alcohol, dodecyl alcohol, 2-ethylhexyl alcohol, pentaerythritol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like. Silicone-based oils such as the polyalkyl-, polyaryl-, polyalkyloxy-, or polyaryloxy-siloxane oils and silicate oils comprise another useful class of synthetic lubricants (e.g., tetraethyl silicate, tetraisopropyl silicate, tetra(2-ethylhexyl)silicate, tetra(4-methyl-2-tetraethyl)silicate, tetra(p-tert-butylphenyl)silicate, hexyl(4-methyl-2-pentoxy)disiloxane, poly(methyl)siloxane, poly(methyl-phenyl)siloxane, etc. Other synthetic lubricating oils include liquid esters of phosphorus-containing acid (e.g., tricresyl phosphate, trioctyl phosphate, diethyl ester of decanephosphonic acid, etc.), polymeric tetrahydrofurans, and the like.

The lubricating oil compositions of this invention comprise a major amount of oil and a minor, load-carrying improving amount of at least one additive composition of the invention. Generally, this amount will be about 0.5 to about 20 parts additive per 100 parts oil.

Exemplary of these lubricating oil compositions are the following:

EXAMPLE 15

A lubricating composition consisting of 98 parts 200 Neutral oil, two parts of the additive composition of Example 6 and 40 parts per million (i.e., ppm) of a commercial silicone-based anti-foam agent.

EXAMPLE 16

A hydraulic fluid composition consisting of 98.95 parts 350 Neutral oil, 1.00 part of the additive composition of Example 6, 0.025 part of an oil solution containing 40% polypropylene tetramer alkenylated succinic acid as a rust inhibitor and 0.025 part of nonylphenoxy poly(ethyleneoxy)ethanol as a demulsifier.

What is claimed is:

1. A process for the preparation of a phosphorus-containing reaction mixture, said mixture comprising at least one additive corresponding to the formula:

$$Y^a\text{-}S\text{-}Y^b$$

wherein $Y^a$ corresponds to

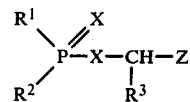

and Z is

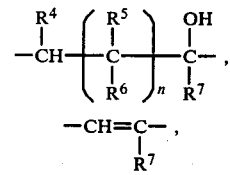

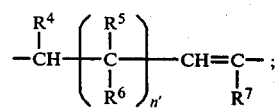

$Y^b$ is $$-R^8\text{-}S\text{-}R^9$$

or $$-R^8\text{-}H$$

which process comprises the steps of reacting
(A) about 0.1 to about 1.0 equivalents of at least one phosphorus-containing reactant corresponding to the formula:

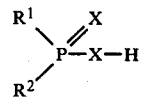

with
(B) about 1.2 to about 0.1 equivalent of at least one unsaturated aldehyde or ketone corresponding to the formula:

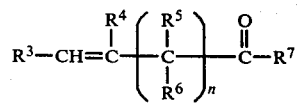

wherein the reaction of (A) and (B) is carried out at a temperature in the range of about 10° C. up to the decomposition point of any component of the reaction mixture and the further reaction of (A) and (B) with
(C) about 1.2 to about 0.1 equivalent of at least one thiol or dithiol corresponding to the formula:

$$HS\text{-}R^8\text{-}H$$

or $$HS\text{-}R^8\text{-}SH$$

wherein the reaction of (A) and (B) with (C) is carried out in the presence of an acid catalyst to prepare the unsaturated phosphorus-containing reaction mixture at a temperature in the range of about 0° C. to about 100°

C. wherein each $R^1$ and $R^2$ is independently a member selected from the group consisting of hydrocarbyl, hydrocarbyloxy and hydrocarbylmercapto of one to about 30 carbon atoms; $R^3$ is hydrogen or hydrocarbyl of up to about 10 carbon atoms; $R^4$ is hydrogen or lower alkyl; $R^5$ and $R^6$ are each independently selected from hydrogen, hydrocarbyl, hydrocarbyloxy and hydrocarbylmercapto of one to about 10 carbon atoms; $R^7$ is hydrogen or hydrocarbyl of one to about 30 carbon atoms; $R^8$ is a divalent hydrocarbyl group of one to about 30 carbon atoms; $R^9$ is hydrogen or $Y^a$; each X is independently oxygen or divalent sulfur; n is zero or an integer of one to about 10 and n' is zero or an integer of one to about 9.

2. The phosphorus-containing reaction mixture produced by the process of claim 1.

3. The reaction mixture according to claim 2 wherein $R^1$ and $R^2$ are each independently hydrocarbyloxy groups containing one to about 30 carbon atoms and each X is oxygen.

4. The reaction mixture according to claim 2 wherein $R^1$ and $R^2$ are each independently hydrocarbyloxy groups containing one to about 30 carbon atoms and each X is a divalent sulfur atom.

5. The reaction mixture according to claim 4 wherein $R^1$ and $R^2$ are each independently alkyloxy or alkylphenoxy groups containing one to about 18 carbon atoms.

6. The reaction mixture according to claim 5 wherein Z is $$-CH\underset{\underset{R^6}{|}}{\overset{\overset{R^4}{|}}{|}}\left(\underset{\underset{R^6}{|}}{\overset{\overset{R^5}{|}}{C}}\right)_n\underset{\underset{R^7}{|}}{\overset{\overset{OH}{|}}{C}}-$$

and $R^3$, $R^4$ and $R^7$ are each independently hydrogen or methyl and n is zero.

7. The reaction mixture according to claim 6 wherein $Y^b$ is $-R^8-S-R^9$ and $R^8$ is a divalent hydrocarbyl group containing one to about 18 carbon atoms and $R^9$ is hydrogen or $Y^a$.

8. The reaction mixture according to claim 7 wherein $R^9$ is $Y^a$.

9. The reaction mixture according to claim 6 wherein $Y^b$ is $-R^8-H$ and $R^8$ is a divalent hydrocarbyl group containing one to about 18 carbon atoms.

10. The reaction mixture according to claim 6 wherein $R^3$ and $R^4$ are each hydrogen, $R^7$ is hydrogen or methyl, $Y^b$ is $-R^8-H$ and $R^8$ is an alkylene group containing about 12 carbon atoms.

11. The reaction mixture according to claim 5 wherein Z is $$-CH=\underset{\underset{R^8}{|}}{C}-$$

and $R^3$ and $R^7$ are each independently hydrogen or methyl.

12. The reaction mixture according to claim 11 wherein $Y^b$ is $-R^8-S-R^9$ and $R^8$ is a divalent hydrocarbyl group containing one to about 18 carbon atoms and $R^9$ is hydrogen or $Y^a$.

13. The reaction mixture according to claim 12 wherein $R^9$ is $Y^a$.

14. The reaction mixture according to claim 11 wherein $Y^b$ is $-R^8-H$ and $R^8$ is a divalent hydrocarbyl group containing one to about 18 carbon atoms.

15. The reaction mixture according to claim 11 wherein $R^3$ is hydrogen, $R^7$ is hydrogen or methyl, $Y^b$ is $-R^8-H$, and $R^8$ is an alkylene group containing about 12 carbon atoms.

16. A concentrate which comprises a substantially inert, normally liquid organic diluent and from about 10% to about 90% of the phosphorus-containing reaction mixture of claim 2 corresponding to the formula:

$$\underset{R^2}{\overset{R^1}{\diagdown}}\overset{\overset{S}{\diagup\!\!\!\diagup}}{P}-S(CH_2)_2-\underset{\underset{R^7}{|}}{\overset{\overset{OH}{|}}{C}}-S-R^8-H$$

wherein $R^1$ and $R^2$ are each independently alkyloxy or alkylphenoxy groups containing about 18 carbon atoms, $R^7$ is hydrogen or methyl and $R^8$ is an alkylene group containing about 12 carbon atoms.

17. A concentrate which comprises a substantially inert, normally liquid organic diluent and from about 10% to about 90% of the phosphorus-containing reaction mixture of claim 2 corresponding to the formula:

$$\underset{R^2}{\overset{R^1}{\diagdown}}\overset{\overset{S}{\diagup\!\!\!\diagup}}{P}-S-CH_2-CH=\underset{\underset{R^7}{|}}{C}-S-R^8-H$$

wherein $R^1$ and $R^2$ are each independently alkyloxy or alkylphenoxy groups containing about 18 carbon atoms, $R^7$ is hydrogen or methyl and $R^8$ is an alkylene group containing about 12 carbon atoms.

* * * * *